(12) United States Patent
Engelhardt et al.

(10) Patent No.: US 9,504,411 B2
(45) Date of Patent: Nov. 29, 2016

(54) DIABETES MANAGER FOR GLUCOSE TESTING AND CONTINUOUS GLUCOSE MONITORING

(75) Inventors: Timothy P. Engelhardt, Avon, IN (US); Gerhard Frisch, Edingen-Neckarhausen (DE); Robert E. Reinke, Indianapolis, IN (US); Wilfried Schmidt, Dannstadt (DE); Michael Schoemaker, Mannheim (DE); Uwe Wittmann, Lampertheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 951 days.

(21) Appl. No.: 13/596,124

(22) Filed: Aug. 28, 2012

(65) Prior Publication Data

US 2014/0066735 A1 Mar. 6, 2014

(51) Int. Cl.
*A61B 5/00* (2006.01)
*A61B 5/145* (2006.01)

(52) U.S. Cl.
CPC .... *A61B 5/14532* (2013.01); *A61B 2560/0209* (2013.01); *A61B 2560/0223* (2013.01)

(58) Field of Classification Search
CPC combination set(s) only.
See application file for complete search history.

(56) References Cited

U.S. PATENT DOCUMENTS

| | | | |
|---|---|---|---|
| 2009/0192380 A1 | 7/2009 | Shariati et al. | |
| 2010/0160759 A1* | 6/2010 | Celentano et al. | 600/365 |
| 2010/0160860 A1* | 6/2010 | Celentano et al. | 604/131 |
| 2010/0185175 A1 | 7/2010 | Kamen et al. | |
| 2010/0292556 A1 | 11/2010 | Golden | |
| 2011/0063094 A1* | 3/2011 | Meiertoberens et al. | 340/12.5 |

OTHER PUBLICATIONS

Seven Continuous Glucose Monitoring System User's Guide, www.DexCom.com, 2010.

* cited by examiner

*Primary Examiner* — Michael Kahelin
*Assistant Examiner* — Mitchell E Alter
(74) *Attorney, Agent, or Firm* — Harness Dickey

(57) ABSTRACT

A handheld diabetes management device for managing blood glucose test data and continuous glucose monitoring data includes a port configured to receive a test strip, a wireless transceiver, a communications processor, and a user interface processor. The communications processor communicates with the wireless transceiver to periodically collect glucose measurement data from a continuous glucose monitoring device and to store the glucose measurement data in a first data storage module. The communications processor is operable to consume electrical power at a first rate. The user interface processor communicates with the communication processor to receive the glucose measurement data and operable to display the glucose measurement data on the device. The communications processor operates asynchronously from operation of the user interface processor to collect the glucose measurement data and the user interface processor operates to consume electrical power at a second rate that is higher than the first rate.

13 Claims, 10 Drawing Sheets

DIABETES MANAGER FOR GLUCOSE TESTING AND CONTINUOUS GLUCOSE MONITORING

FIELD

The present disclosure relates to a handheld diabetes manager in communication with a continuous glucose monitoring device.

BACKGROUND

Diabetes mellitus, often referred to as diabetes, is a chronic condition in which a person has elevated blood glucose levels that result from defects in the body's ability to produce and/or use insulin. There are three main types of diabetes. Type 1 diabetes usually strikes children and young adults, and may be autoimmune, genetic, and/or environmental. Type 2 diabetes accounts for 90-95% of diabetes cases and is linked to obesity and physical inactivity. Gestational diabetes is a form of glucose intolerance diagnosed during pregnancy and usually resolves spontaneously after delivery.

Diabetes is managed primarily by controlling the level of glucose in the bloodstream. This level is dynamic and complex, and is affected by multiple factors including the amount and type of food consumed, and the amount of insulin (which mediates transport of glucose across cell membranes) in the blood. Blood glucose levels are also sensitive to exercise, sleep, stress, smoking, travel, illness, menses, and other psychological and lifestyle factors unique to individual patients. The dynamic nature of blood glucose and insulin, and all other factors affecting blood glucose, often require a person with diabetes to forecast blood glucose levels. Therefore, therapy in the form of insulin or oral medications, or both, can be timed to maintain blood glucose levels in an appropriate range.

Management of diabetes is time-consuming for patients because of the need to consistently obtain reliable diagnostic information, follow prescribed therapy, and manage lifestyle on a daily basis. Diagnostic information, such as blood glucose, is typically obtained from a capillary blood sample with a lancing device and is then measured with a handheld blood glucose meter. Interstitial glucose levels may be obtained from a continuous glucose sensor worn on the body. Prescribed therapies may include insulin, oral medications, or both. Insulin can be delivered with a syringe, an ambulatory infusion pump, or a combination of both. With insulin therapy, determining the amount of insulin to be injected can require forecasting meal composition of fat, carbohydrates and proteins along with effects of exercise or other physiologic states. The management of lifestyle factors such as body weight, diet, and exercise can significantly influence the type and effectiveness of a therapy.

Management of diabetes involves large amounts of diagnostic data and prescriptive data acquired in a variety of ways: from medical devices, from personal healthcare devices, from patient-recorded logs, from laboratory tests, and from healthcare professional recommendations. Medical devices include patient-owned bG meters, continuous glucose monitors, ambulatory insulin infusion pumps, diabetes analysis software, and diabetes device configuration software. Each of these systems generates and/or manages large amounts of diagnostic and prescriptive data. Personal healthcare devices include weight scales, blood pressure cuffs, exercise machines, thermometers, and weight management software. Patient recorded logs include information relating to meals, exercise and lifestyle. Lab test results include HbA1C, cholesterol, triglycerides, and glucose tolerance. Healthcare professional recommendations include prescriptions, diets, test plans, and other information relating to the patient's treatment.

Patients using continuous glucose monitoring (CGM) devices or patches generally review summaries of the fluctuations in their glucose values for particular time intervals ranging from hours to days. In particular, a patient wears a CGM device that can communicate with a handheld device such as a CGM manager. The present teachings are directed to various methods of processing and managing bG tests and glucose data from a CGM patch using a handheld diabetes manager.

SUMMARY

This section provides a general summary of the disclosure, and is not a comprehensive disclosure of its full scope or all of its features.

The present teachings provide a handheld diabetes management device for managing blood glucose test data and continuous glucose monitoring data includes a port configured to receive a test strip, a wireless transceiver, a communications processor, and a user interface processor. The communications processor communicates with the wireless transceiver to periodically collect glucose measurement data from a continuous glucose monitoring device and to store the glucose measurement data in a first data storage module. The communications processor is operable to consume electrical power at a first rate. The user interface processor communicates with the communication processor to receive the glucose measurement data and operable to display the glucose measurement data on a display of the device. The communications processor operates asynchronously from operation of the user interface processor to collect the glucose measurement data and the user interface processor operates to consume electrical power at a second rate that is higher than the first rate.

In some embodiments the communication processor is operable to detect an error condition related to a continuous glucose measurement data or the collection thereof. The communication processor invokes the user interface processor immediately to report the error condition to the interface processor upon detecting an error condition of a first type but defers reporting the error condition to the user interface processor upon detecting an error condition of a second type different than the first type. The first type of error condition includes a status of active (enabled) safety warnings and any of: a warning threshold is crossed, a recommendation to calibrate state, a communication error in the transceiver or communications processor; loss of communication with the continuous glucose monitoring device, and a non-zero status from the continuous glucose monitoring device. The second type of error condition includes a status of non-active (disabled) safety warnings and any of the following events: a recommendation to calibrate, a communication error in the transceiver or communications processor, and a non-zero status from the continuous glucose monitoring device. The user interface processor is in data communication with the communication processor to receive the glucose measurement data and is operable to display the glucose measurement data on a display of the device. The user interface processor is configured to operate in a low power mode, and enters an active mode upon receipt of the error condition from the communication processor and generates an error notification in response to the error condition received from the communication processor. The user interface processor consumes electrical power in the active mode at a higher rate than in the low power mode.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
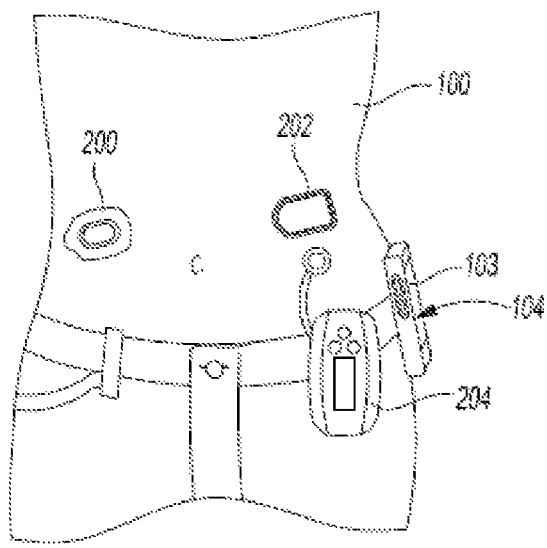
FIG. 1 shows a patient with a continuous glucose monitoring (CGM) patch, an ambulatory durable insulin infusion pump, an ambulatory non-durable insulin infusion pump, and a diabetes manger.

The following description is merely illustrative in nature and is in no way intended to limit the disclosure, its application, or uses. For purposes of clarity, the same reference numbers will be used in the drawings to identify similar elements. As used herein, the phrase at least one of A, B, and C should be construed to mean a logical (A or B or C), using a non-exclusive logical or. It should be understood that steps within a method may be executed in different order without altering the principles of the present disclosure.

Referring now to FIG. 1, a person with diabetes 100 using various medical devices is illustrated. Persons with diabetes include persons with metabolic syndrome, persons with pre-diabetes, type 1 diabetics, type 2 diabetics, and gestational diabetics and are collectively referred to as a patient. Healthcare providers for diabetes are diverse and include nurses, nurse practitioners, physicians, and endocrinologists and are collectively referred to as a clinician.

During a healthcare consultation, the patient 100 typically shares with the clinician a variety of patient data including blood glucose measurements, continuous glucose monitor data, amounts of insulin infused, amounts of food and beverages consumed, exercise schedules, and other lifestyle information. The clinician may obtain additional patient data that includes measurements of HbA1C, cholesterol levels, triglycerides, blood pressure, and weight of the patient 100. The patient data can be recorded manually or electronically on a handheld diabetes management device 104 having a display 103, a diabetes analysis software executed on a personal computer (PC), and/or a web-based diabetes analysis site (not shown). The clinician can analyze the patient data manually or electronically using the diabetes analysis software and/or the web-based diabetes analysis site. After analyzing the patient data and reviewing adherence of the patient 100 to previously prescribed therapy, the clinician can decide whether to modify the therapy for the patient 100.

Referring now to FIG. 1, the patient 100 can use a continuous glucose monitoring (CGM) device or CGM patch 200, an ambulatory non-durable insulin infusion pump 202 or an ambulatory durable insulin infusion pump 204 (hereinafter insulin pump 202 or 204), and the handheld diabetes management device 104 (hereinafter the diabetes manager or meter 104). The CGM patch 200 includes a body mount, a reusable component and a subcutaneous sensor to sense and monitor the amount of glucose in interstitial fluid of the patient 100 and communicates corresponding data to the diabetes manager 104.

The diabetes manager 104 can performs various tasks including measuring and recording blood glucose levels, determining an amount of insulin to be administered to the patient 100 via the insulin pump 202 or 204, receiving patient data via a user interface, archiving the patient data, etc. The diabetes manager 104 periodically receives data from the CGM patch 200 from which glucose levels of the patient 100 are computed. The diabetes manager 104 transmits instructions to the insulin pump 202 or 204, which delivers insulin to the patient 100. Insulin can be delivered in a scheduled manner in the form of a basal dose, which maintains a predetermined insulin dose to the patient 100. Additionally, insulin can be delivered in the form of a bolus dose, which raises the amount of insulin delivered to the patient 100 by a predetermined amount.

The CGM patch 200 can be generally used to obtain time-resolved data to identify fluctuations and trends that would otherwise go unnoticed with spot monitoring of blood glucose levels and standard HbA1c tests, such as low overnight glucose levels, high blood glucose levels between meals, early morning spikes in blood glucose levels, and how diet and physical activity affect blood glucose along with the effect of therapy changes. An example of a CGM patch 200 is shown in U.S. Pat. No. 7,389,133 assigned to Roche Diagnostics Operations, Inc., which is hereby incorporated by reference.

Generally, glucose data may be transmitted from the CGM patch 200 on demand, or substantially continuously whenever a measurement is carried out by the CGM patch 200, for example, every minute or every few minutes. Alternatively, the CGM patch 200 may include a memory and temporarily store measured CGM glucose values which are subsequently transmitted to the diabetes manager 104. For example, the stored values may be transmitted when the memory of the CGM patch 200 is full, or when a communication is established for other reasons, or in pre-defined time intervals. The CGM patch 200 may communicate with the diabetes manager 104 wirelessly via an RF data interface, for example short range RF data interfaces based on the Bluetooth standard.

Although a sensor of the CGM patch 200 may take measurements every second, the sixty data points measured within a minute timeframe can be compressed by taking either the mean or median or other characteristic value of the sixty measurements. Other useful parameters for the minute time range may also be calculated in the CGM patch 200, including the standard deviation and other trends. The raw data may also be filtered to remove noise or other non-physiological spikes in the data. The compressed and/or filtered data corresponding to each minute, i.e., the characteristic value for each minute, are then transferred to diabetes manager 104 as described below.

Figure 2:
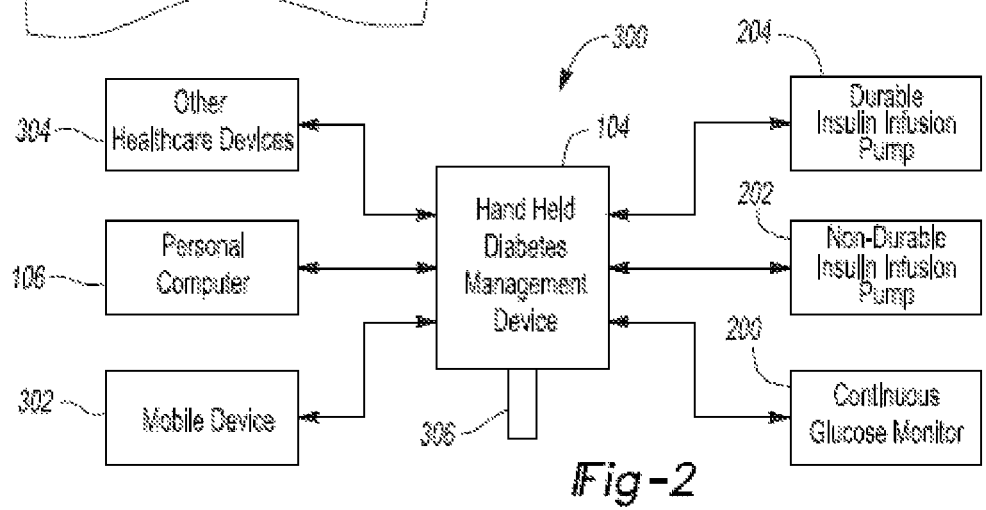
FIG. 2 shows a diabetes management system used by patients and clinicians to manage diabetes.

Generally, and referring now to FIG. 2, a diabetes management system 300 used by the patient 100 and the clinician can include one or more of the following devices: the diabetes manager 104, the continuous glucose monitor (CGM patch) 200, the insulin pump 202 or 204, a mobile device 302, the PC 106 with diabetes analysis software, and other healthcare devices 304. The diabetes manager 104 is configured as a system hub and communicates with the devices of the diabetes management system 300. Alternatively, the mobile device 302 can serve as the system hub. Communication between the devices in the diabetes management system 300 can be performed using wireless interfaces (e.g., Bluetooth) and/or wired interfaces (e.g., USB). Communication protocols used by these devices can include protocols compliant with the IEEE 11073 standard, as extended using guidelines provided by Continua® Health Alliance Design Guidelines. Further, healthcare records systems such as Microsoft® HealthVault™ and Google™ Health can be used by the patient 100 and clinician 102 to exchange information.

The diabetes manager 104 can receive glucose readings from one or more sources (e.g., from the CGM patch 200). The CGM patch 200 continuously monitors the glucose level of the patient 100. The CGM patch 200 periodically communicates data to the diabetes manager 104 from which the diabetes manager 104 computes glucose levels of the patient. The diabetes manager 104 and the CGM patch 200 communicate wirelessly using generally a proprietary wireless protocol, such as, for example, the Gazell wireless protocol developed by Nordic Semiconductor, Inc., Sunnyvale, Calif. Any other suitable wireless protocol can be used instead.

Additionally, the diabetes manager 104 includes a blood glucose meter (BGM) and a port that communicates with the BGM (not shown). The port can receive a blood glucose measurement strip 306. The patient 100 deposits a sample of blood on the blood glucose measurement strip 306. The BGM analyzes the sample and measures the blood glucose level in the sample. The blood glucose level measured from the sample and/or the glucose level computed using data received from the CGM patch 200 can be used to determine the amount of insulin to be administered to the patient 100.

The diabetes manager 104 can also communicate with the insulin pump 202 or 204. The insulin pump 202 or 204 can be configured to receive instructions from the diabetes manager 104 to deliver a predetermined amount of insulin to the patient 100. Additionally, the insulin pump 202 or 204 can receive other information including meal and/or exercise schedules of the patient 100. The insulin pump 202 or 204 can determine the amount of insulin to administer based on the additional information.

The insulin pump 202 or 204 can also communicate data to the diabetes manager 104. The data can include amounts of insulin delivered to the patient 100, corresponding times of delivery, and pump status. The diabetes manager 104 and the insulin pump 202 or 204 can communicate using a wireless communication protocol such as Bluetooth. Other wireless or wired communication protocols can also be used.

In addition, the diabetes manager 104 can communicate with the other healthcare devices 304. For example, the other healthcare devices 304 can include a blood pressure meter, a weight scale, a pedometer, a fingertip pulse oximeter, a thermometer, etc. The other healthcare devices 304 obtain and communicate personal health information of the patient 100 to the diabetes manager 104 through wireless, USB, or other interfaces. The other healthcare devices 304 may use communication protocols compliant with ISO/IEEE 11073 extended using guidelines from Continua® Health Alliance. The diabetes manager 104 can communicate with the other healthcare devices 304 using interfaces including Bluetooth, USB, etc. Further, the devices of the diabetes management system 300 can communicate with each other via the diabetes manager 104.

The diabetes manager 104 can communicate with the PC 106 using Bluetooth, USB, or other interfaces. A diabetes management software running on the PC 106 includes an analyzer-configurator that stores configuration information of the devices of the diabetes management system 300. The configurator has a database to store configuration information of the diabetes manager 104 and the other devices. The configurator can communicate with users through standard web or computer screens in non-web applications. The configurator transmits user-approved configurations to the devices of the diabetes management system 300. The analyzer retrieves data from the diabetes manager 104, stores the data in a database, and outputs analysis results through standard web pages or computer screens in non-web based applications.

The diabetes manager 104 can communicate with the mobile device 302 using Bluetooth. The mobile device 302 may include a cellular phone, a pager, or a personal digital assistant (PDA). The diabetes manager 104 can send messages to an external network through the mobile device 302. The mobile device 302 can transmit messages to the external network upon receiving requests from the diabetes manager 104.

Figure 3:
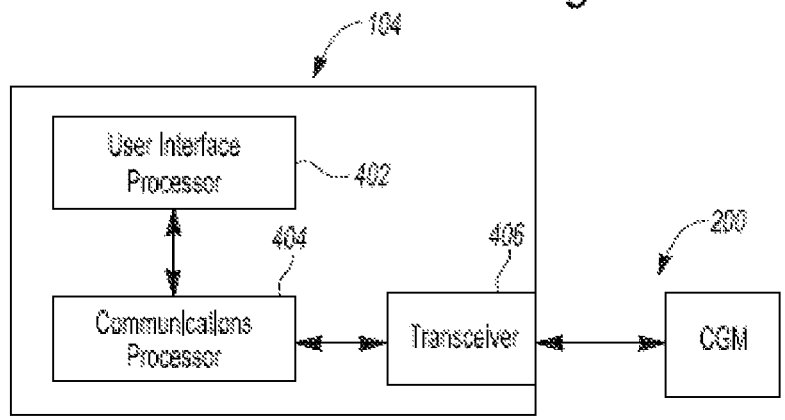
FIG. 3 is a functional block diagram of a diabetes manager according to the present teachings.
Figure 4:
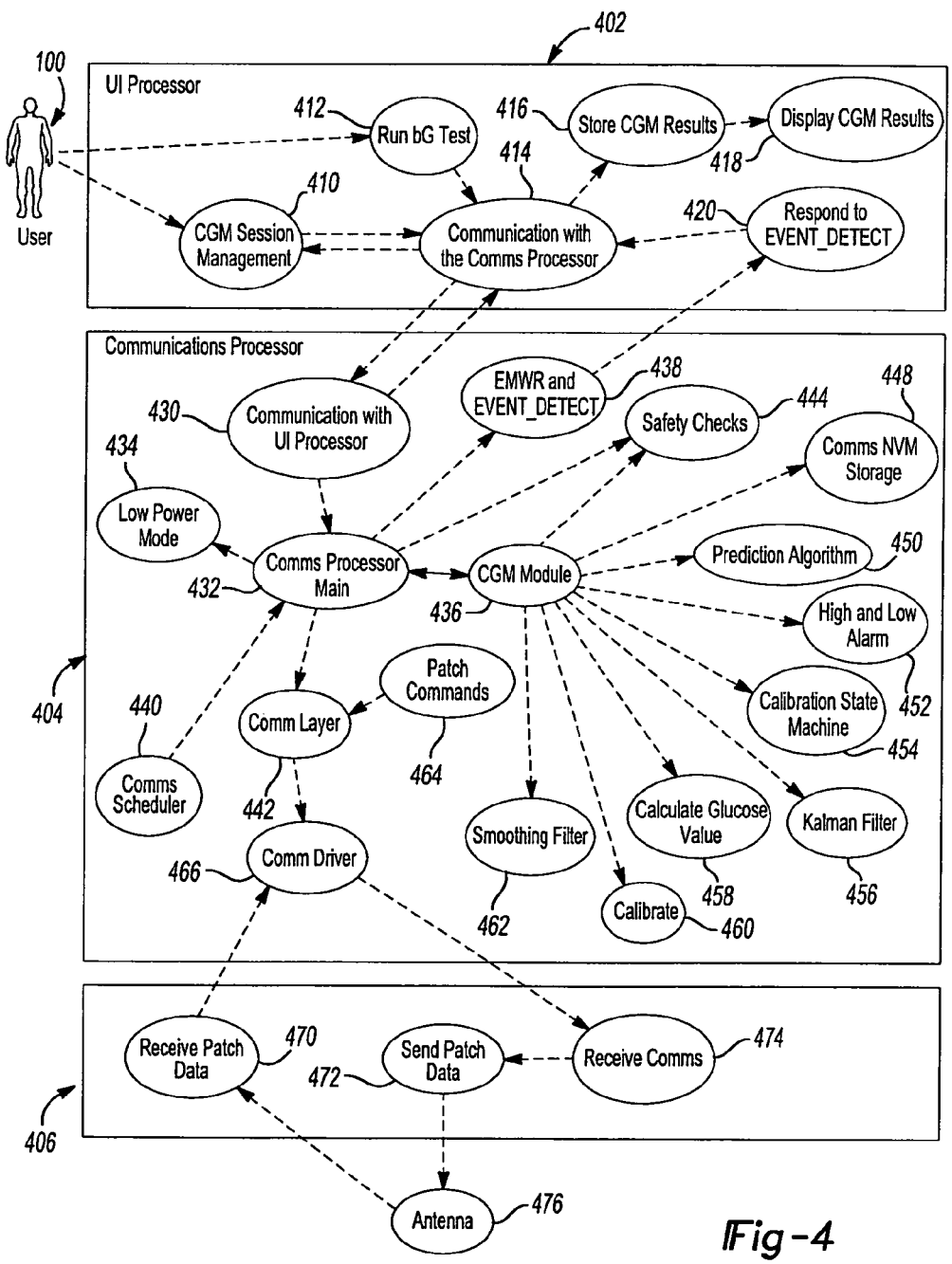
FIG. 4 is a schematic functional diagram of the diabetes manager of FIG. 3.

Referring to FIGS. 3-10, the diabetes manager 104 will be particularly described in relation to the processes, management of data and interaction with a continuous glucose monitoring device, such as the CGM patch 200 and/or other related devices. Referring to FIGS. 3 and 4, the diabetes manager 104 of the present teachings includes two separate processors (or controllers), i.e., a user interface processor 402 and a communications processor 404, and a wireless transceiver 406 that communicates with the communications processor 404 and the CGM patch 200. The communications processor 404 can be a microprocessor or microcontroller with lower power requirements than the power requirements of the user interface processor 402, as will be discussed below. The user interface processor 402 can be, for example, a processor manufactured by Freescale Semiconductors, Inc., Austin, Tex., and the communications processor can be a STM32 processor manufactured by STMicroelectronics, Coppell, Tex., although other processors known in the art can be also used.

The various processes, functions, software modules, codes or commands that are performed in the user interface (UI) processor 402, the communications processor 404 and the wireless transceiver 406 are illustrated schematically in the diagram of FIG. 4 and will be referenced for simplicity as "modules". An overview of the various modules and function of the UI processor 402, the communications processor 404 and the wireless transceiver 406 is first presented below in reference to FIG. 4 before detailed flow diagrams are described later in reference to FIGS. 5-10

Specifically, the user interface processor 402 includes a CGM Session Management module 410, a bG Test module 412, a Communications Processor Communication module 414, a CGM Results Storage module 416, a CGM Results Display module 418 and an Event Detection Response module 420. It is noted that the above list of modules is not complete, as only the modules substantially related to the present teaching are described. The UI processor 402, for example, can include other modules related to bG and CGM data processing and other bG meter functions of the diabetes manager 104, including graphical representation of data, user diary, food databases, scheduling of tests, time alerts, etc.

The CGM Session Management module 410 receives a command from the UI processor 402 to initiate a new CGM session when the CGM patch 200 has just been paired and the diabetes manager 104 needs to be updated with this information. The CGM Session Management module 410 performs the tasks of completing pairing with the CGM patch 200, preparing the communications processor 404 for the new CGM session (including the start time of the CGM session to the CGM patch) and requesting the record of the data stored in the memory of the CGM patch 200 (such as for example, the five most current readings of the CGM patch). Additionally, CGM Session Management module 410 manages the ending of the CGM session, ensures that all the minute data and the background data has been retrieved from the CGM patch 200 before the CGM session ends, and ensures that all data has been recovered from the CGM patch 200 and the communications processor 404.

The UI processor 402 includes a blood glucose measuring engine that analyzes samples provided by the patient 100 on the blood glucose measurement strip 306 and that measures the amount of blood glucose in the samples. Additionally, the bG Test Module 412 is configured to process bG test results during a CGM session. Specifically, when a bG test is run during a CGM session, a determination is made and indicated to the user 100 on whether the bG test can be used to calibrate the CGM patch 200. Calibration can be made if the following tasks are completed: all the data have been received from the CGM patch 200 and have been processed by the communications processor 404; the bG result was sent to the communications processor 404; and the communications processor 404 determined that it can use the bG result to calibrate, and notified the UI processor 402. The UI processor then indicates to the user 100 that the bG test can be used to calibrate the CGM patch 200. If the communications processor 404 cannot use the bG test result for calibration, it will return the reason to the UI processor 402. The Communications Processor Communication module 414 handles the communications between the UI processor 402 and the communications processor 404.

With continued reference to FIG. 4, the Event Detection Response module 420 corresponds to an "EMWR" and Event Detect module 438 in the communications processor 404. "EMWR" is used inclusively for error, maintenance, warnings and reminders, but it can be any event message or event notification. The notification itself is shown in the illustrative flowcharts of FIGS. 6 and 7, for example, as "Event Detect" notification. The Event Detect Response module 420 is used to query the communications processor 404 about the nature and the reason for an Event Detect notification and trigger received by the communications processor. As will be discussed below in connection with the function of the communications processor 404, the communications processor 404 performs certain operations that are not in direct response to a command from the UI processor 402. If, during the performance of these operations, the communication processor 404 encounters an error, requires assistance or information from the UI processor 402, the communications processor 404 asserts an Event Detect notification to the UI processor 402.

The UI processor 402 also includes the CGM Results Storage module 416 that is the permanent storage for CGM data, including raw data and calculations and results after the CGM data are processed by the diabetes manager 104 in the UI processor by other modules of the UI processor 402. The CGM data stored in the CGM Results Storage module 416 can be displayed to the user via the CGM Results Display module 418. The CGM data may be compacted in order to display data for multiple days to the user.

With continued reference to FIG. 4, functions and/or modules of the communications processor 404 are described to the extent that they relate to present teachings and to interaction of the diabetes manager 104 with the CGM patch 200. It is noted that that other modules that are not necessary for the description of the present teachings may not be described and/or shown herein. The communications processor 404 includes a Communication With UI Processor module 430, a Communications Processor Main module 432; a Low Power Mode module 434, a CGM module 436 and a Communications Scheduler module 440. The Communication With UI Processor module 430 handles all the communications between the UI processor 402 and the Communications Processor Main module 432 that serves as the main hub of the CGM-related activities of the communications processor 404. The Communications Processor Main module 432 interacts with the CGM module 436 and routes CGM related commands for the CGM module 436.

The CGM module 436 functions as the state machine for CGM algorithms or subroutines. Although many of these algorithms are interrelated, they are shown as separate modules in FIG. 4 for easier identification. Parts of the algorithms may be either performed or bypassed depending on various variables, such as the availability of appropriate calibration coefficients, age of the data and what warnings are enabled in the user interface of the diabetes manager 104.

The CGM module 436 includes or interacts with a Calibration State Machine module 454, a Prediction Algorithm Module 450, a High and Low Alarm module 452, a Kalman Filter module 456, a Glucose Value Calculation Module 458, a Smoothing Filter module 462, a Calibrate module 460, a Safety Checks module 444 and a Communications NVM Storage module 448. The Smoothing Filter module 462 is first applied to the raw data (raw currents) from the CGM patch 200 to reduce noise from the data. After the raw data are processed by the Smoothing Filter module 462, the Glucose Value Calculation module 458 applies calibration coefficients to the raw currents to obtain corresponding glucose values. Calibration coefficients that are too old cannot be used to calculate glucose values. The length of time the calibration coefficients can be used is a parameter in a data memory (SROM) module of the CGM patch 200. The Calibration State Machine module 454 has two states "recommend calibrate" and "do not calibrate" which can be accessed for further action regarding a CGM session of the CGM patch 200. If the state or status returns a value or response of "recommend calibrate", the data will pass through the Calibrate module 460. If the state is and remains as "do not calibrate" for a time period defined by the SROM of the CGM patch 200, then the CGM session is terminated whether the UI processor 402 is in standby or active mode. The Kalman Filter module 456 receives the previously calculated glucose values and filters the glucose values. The filtered glucose values are used in the remaining modules and calculations/functions of the CGM module 436.

The Prediction Algorithm Module 450 operates to predict a hyperglycemia or hypoglycemia condition. The High and Low Alarm module 452 operates to provide warnings to the UI processor 402 via the CGM module when the filter algorithm indicates that the glucose value of the user 100 is in a warning condition, when such warnings are enabled. The warning condition may occur whether the UI processor 402 is in standby or active mode. After the CGM data has passed through all the required algorithms, the raw data and associated calculated or processed data are stored in a Communications NVM Storage module 448, which is the nonvolatile memory storage of the communications processor 404. The communications processor includes an EEPROM-type of memory which is erasable by electrical charge and retains its contents when the power is off. The Communications NVM Storage module 448 stores only a limited amount CGM data at a time, while the UI processor 402 stores most of the CGM data in the CGM Results Storage module 416.

The communications processor 404 includes an EMWR and Event Detect module 438. EMWR is shorthand for error, maintenance, warnings and reminders. All EMWR events that occur in the communications processor 404 are reported to the UI processor 402 using Event Detect condition and are stored or displayed to the user 100 as appropriate. Two types of EMWR events are defined. The first type corresponds to solicited error events that are caused by the failure of the communications processor 404 to execute a command. This failure is handled with a response to the command and the UI processor 402 may have to issue several other commands to determine a complete picture of the failure. The second-type corresponds to unsolicited error events in the communications processor 404. In response to this type of error, the UI processor 402 queries the communications processor 404 to determine the cause of the event. The Event Detect condition is de-asserted in preparation for the next instance of this type of EMWR event.

The communications processor 404 also includes a Patch Commands module 464 that handles commands for the CGM patch 200. The commands are transferred to a Communications Layer module 442, which receives all the data to be transmitted to the CGM patch 200 via the wireless transceiver 406. A Communications Scheduler module 440 interacts with the Communications Processor Main module 432 to schedule transmittal first through the Communications Layer module 442 and then to a Communications Driver 466. The Communications Driver 466 sends commands to a Receive Commands module 474 of the transceiver 406 and receives CGM patch data from a Receive Patch Data module 470 of the transceiver 406. The transceiver includes a Send Patch Data module 472 that transfers patch data to an antenna 476 for wireless transmission to the CGM patch 200. Patch data from the antenna 476 are received by the Receive Patch Data module 470 and sent to the Communications Driver 466.

The Communications Processor Main module 432 routes any commands intended for CGM functions to the CGM module 436. When the CGM module 436 identifies a need to notify the UI processor 402 regarding an Event Detect assertion, it notifies the Communications Processor Main module 432 that asserts the Event Detect event, as appropriate. When the query Event Detect command is received from the UI processor 402, the Communications Processor Main module 432 handles the response if it can or gets information from CGM module 436 as needed. When the communications processor 404 is put in sleep mode, the Communications Processor Main module 432 must understand the state of the CGM module 436 so that the proper wakeup resources can be set up. Safety checks are done before the CGM module 436 is called in a Safety Checks module 444, and other safety checks are done within the CGM algorithm flow described above. Because gathering all of the necessary information from the CGM patch 200 can take a measurable amount of time, care is taken to perform communication, calculations, and storing of the data as quickly as possible. Time slicing rules are followed, as there may be hours of minute data that could take 30 seconds to download from the CGM patch 200. Time slicing rules are implemented so that other tasks are not starved out.

The communications processor 404 also includes a Low Power Mode module 434. The communications processor 404 and more generally the diabetes manager 104 can be in a standby or sleep mode to conserve power and extend battery life of the diabetes manager 104. The Low Power module manages the wake up functions. For example, if the data from the CGM patch 200 needs to be downloaded to the communications processor 404 while the diabetes manager 104 is in standby mode, a timer is set to wake up the communications processor 404 at the desired interval. During a CGM session, the UI processor 402 may need to send a command to wake up the communications processor 404 to allow the CGM module 436 to know what is happening in the UI processor 402. This command could be a command to begin communication with the CGM patch 200 or stop communication with the CGM patch 200.

The diabetes manager 104 generally includes a rechargeable battery. The battery can be recharged using an adapter that plugs into a wall outlet. The battery can also be charged via a USB port of the diabetes manager 104. The communications processor 404 operates to consume electrical power at a first rate and the UI processor operates to consume power at a second rate that is higher than the first rate. The operation of the communications processor 404 to collect and process glucose data is asynchronous relative to the operation of the UI processor 402. Both the communications processor 404 and the UI processor 402 have an active mode and a standby or sleep mode, which is a lower power mode, such that they consume electrical power in the active mode at a higher rate than in the low power mode.

Figure 5A:
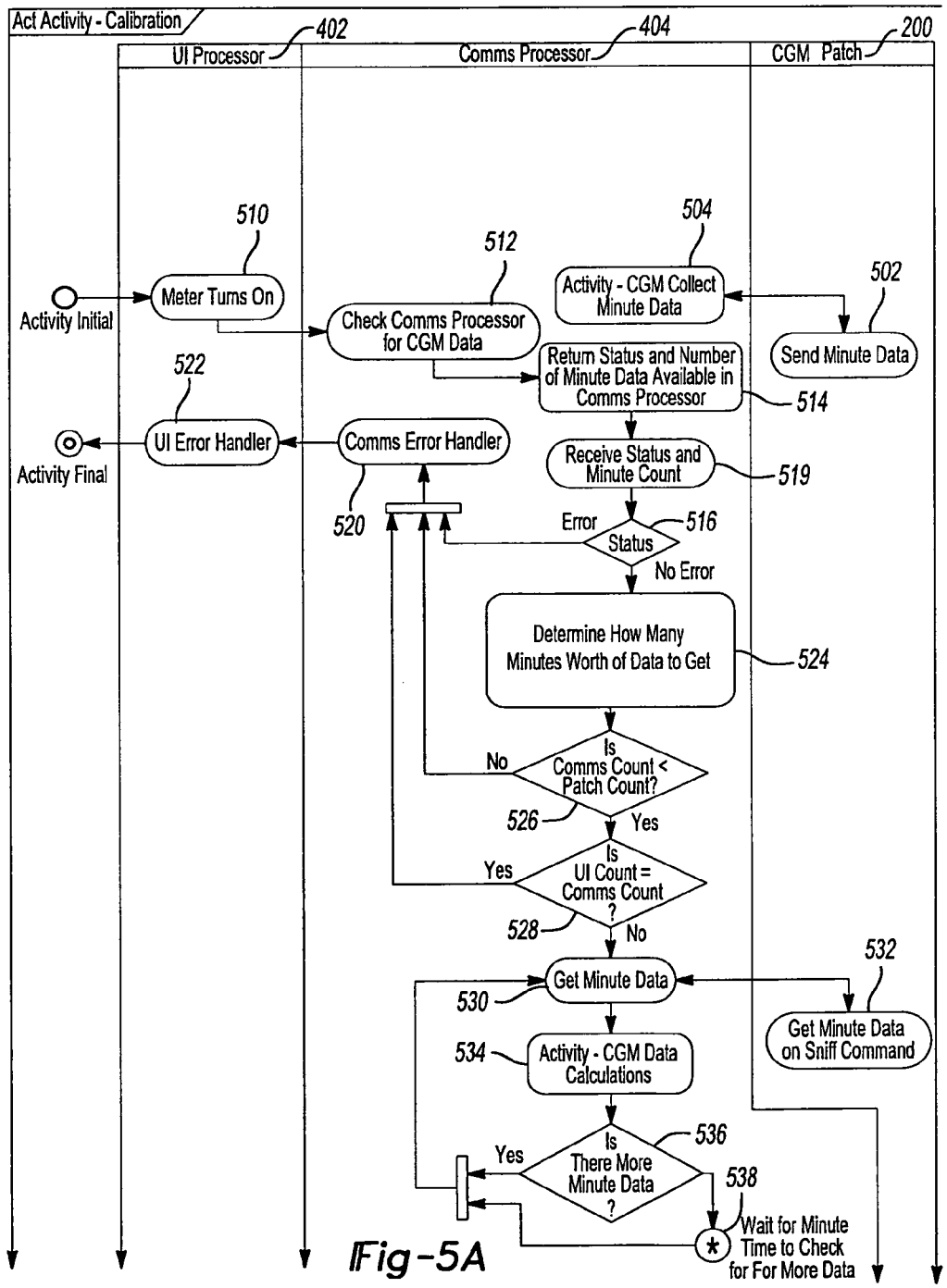
FIG. 5 (shown as FIG. 5A and FIG. 5B) is a functional flow diagram of a calibration activity of the diabetes manager of FIG. 3.
Figure 5B:
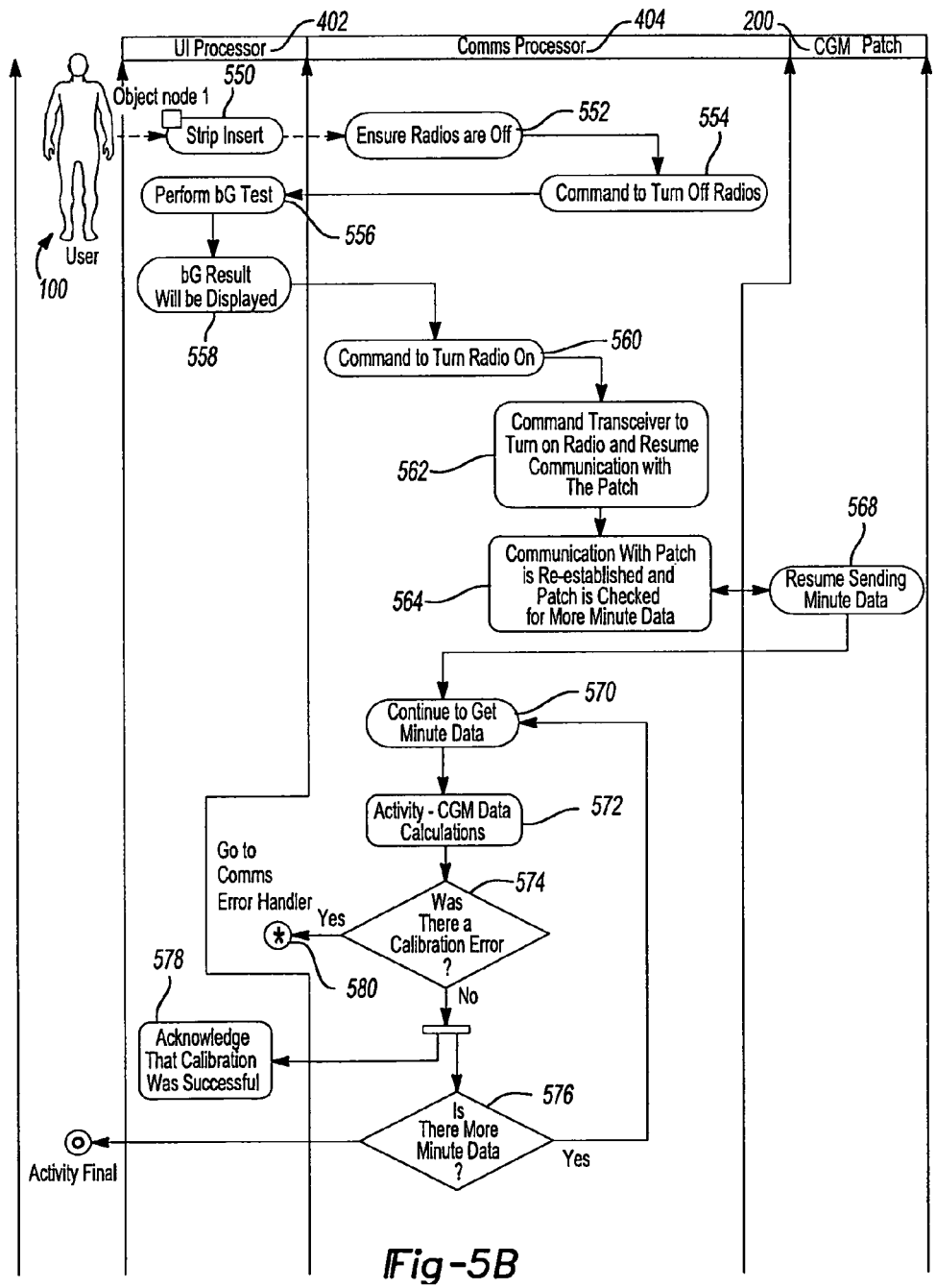
Figure 6:
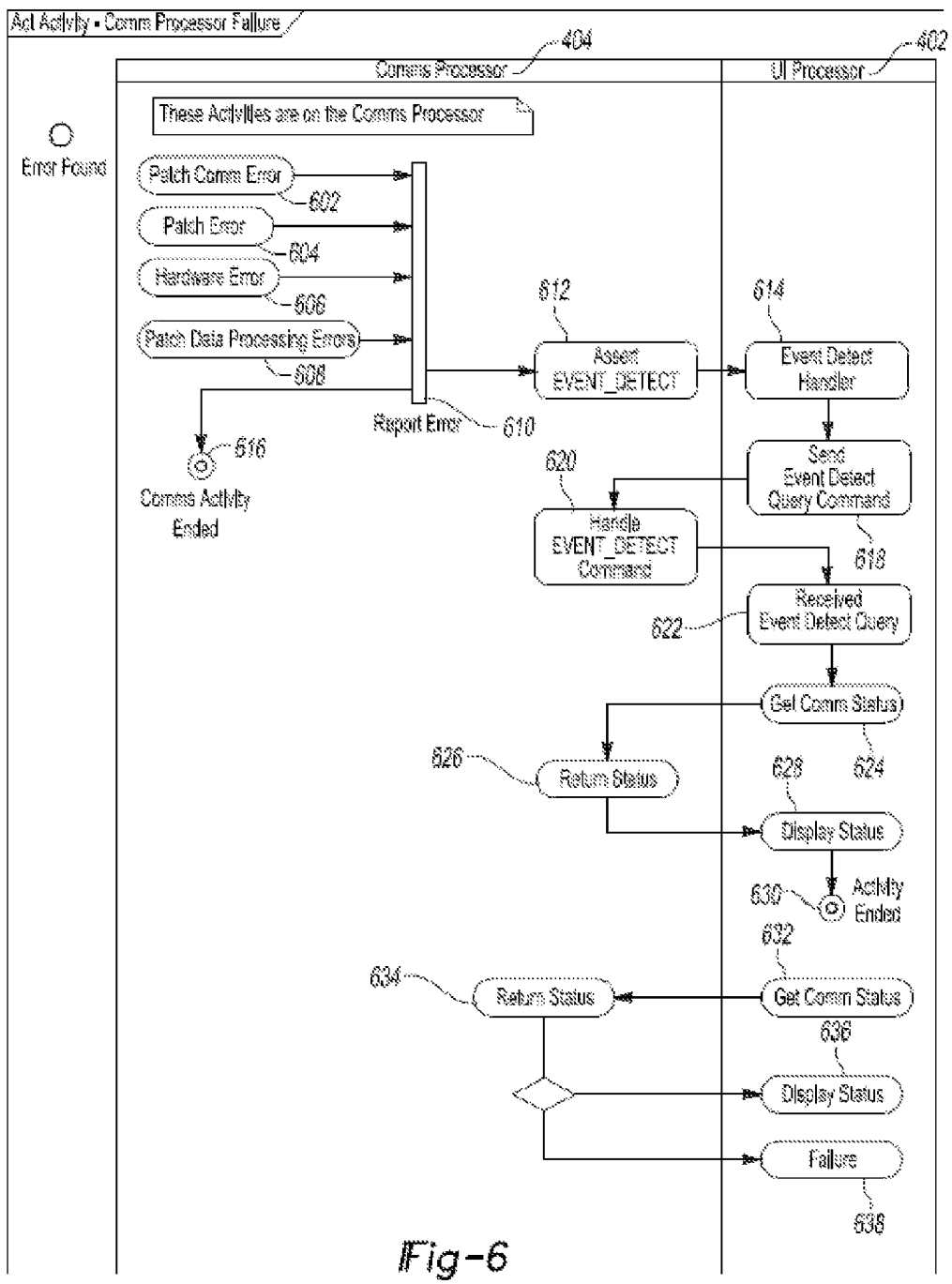
FIG. 6 is a functional flow diagram of an activity related to a communication processor failure of the diabetes manager of FIG. 3.
Figure 7:
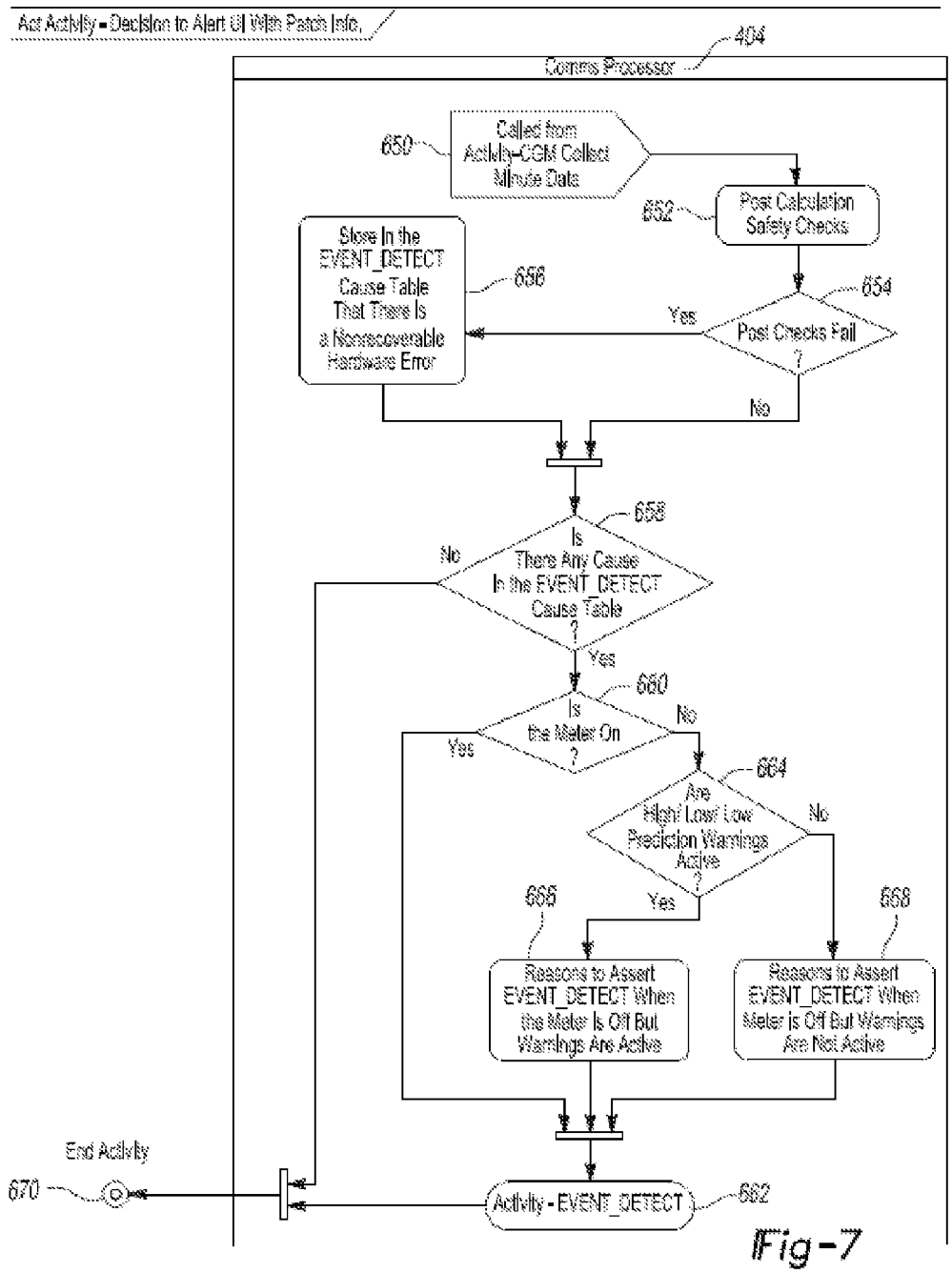
FIG. 7 is a functional flow diagram of an activity related to a decision to alert a user interface processor of the diabetes manager of FIG. 3.
Figure 8:
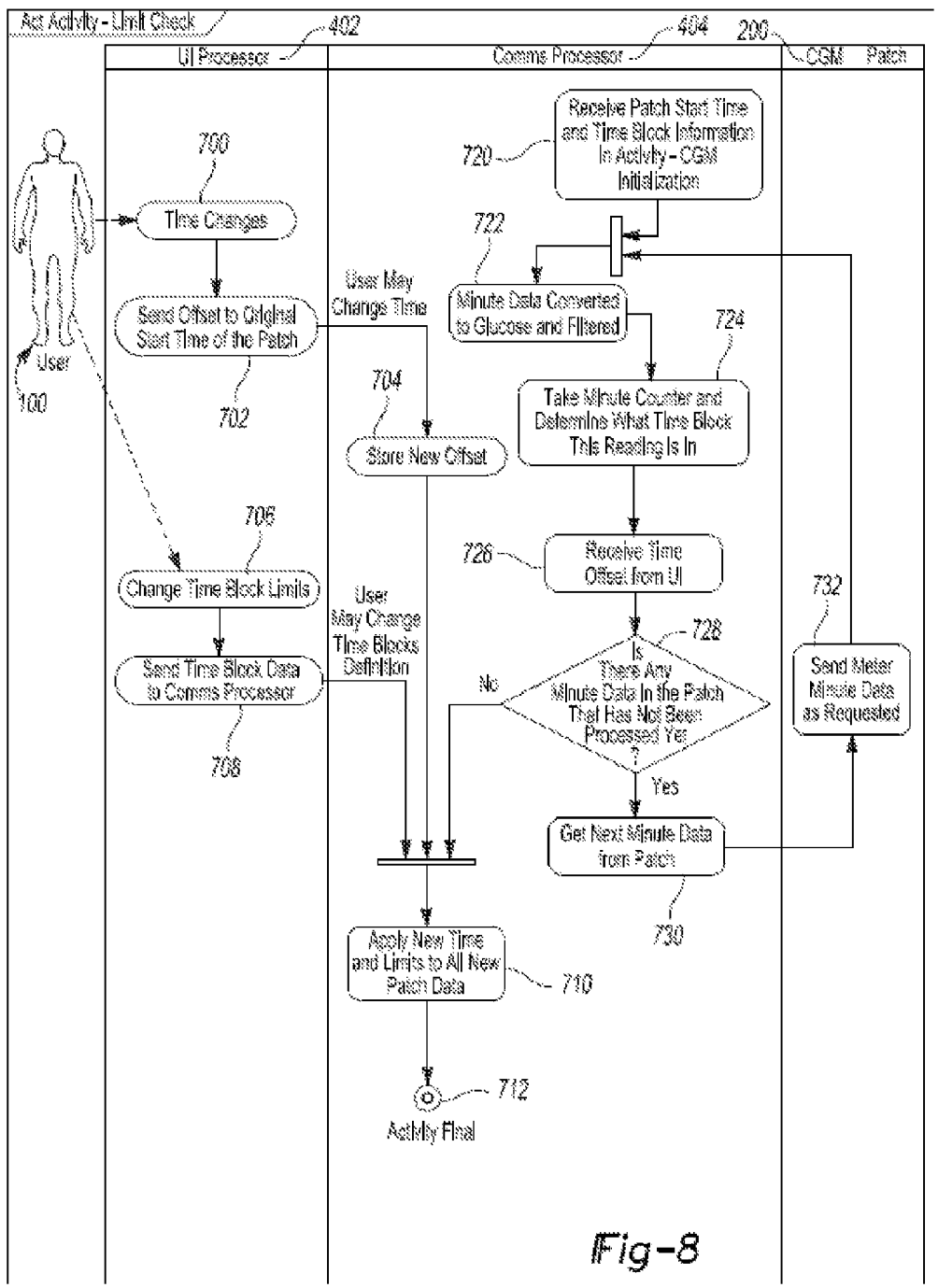
FIG. 8 is a functional flow diagram of an activity related to limit checks of the diabetes manager of FIG. 3.
Figure 9:
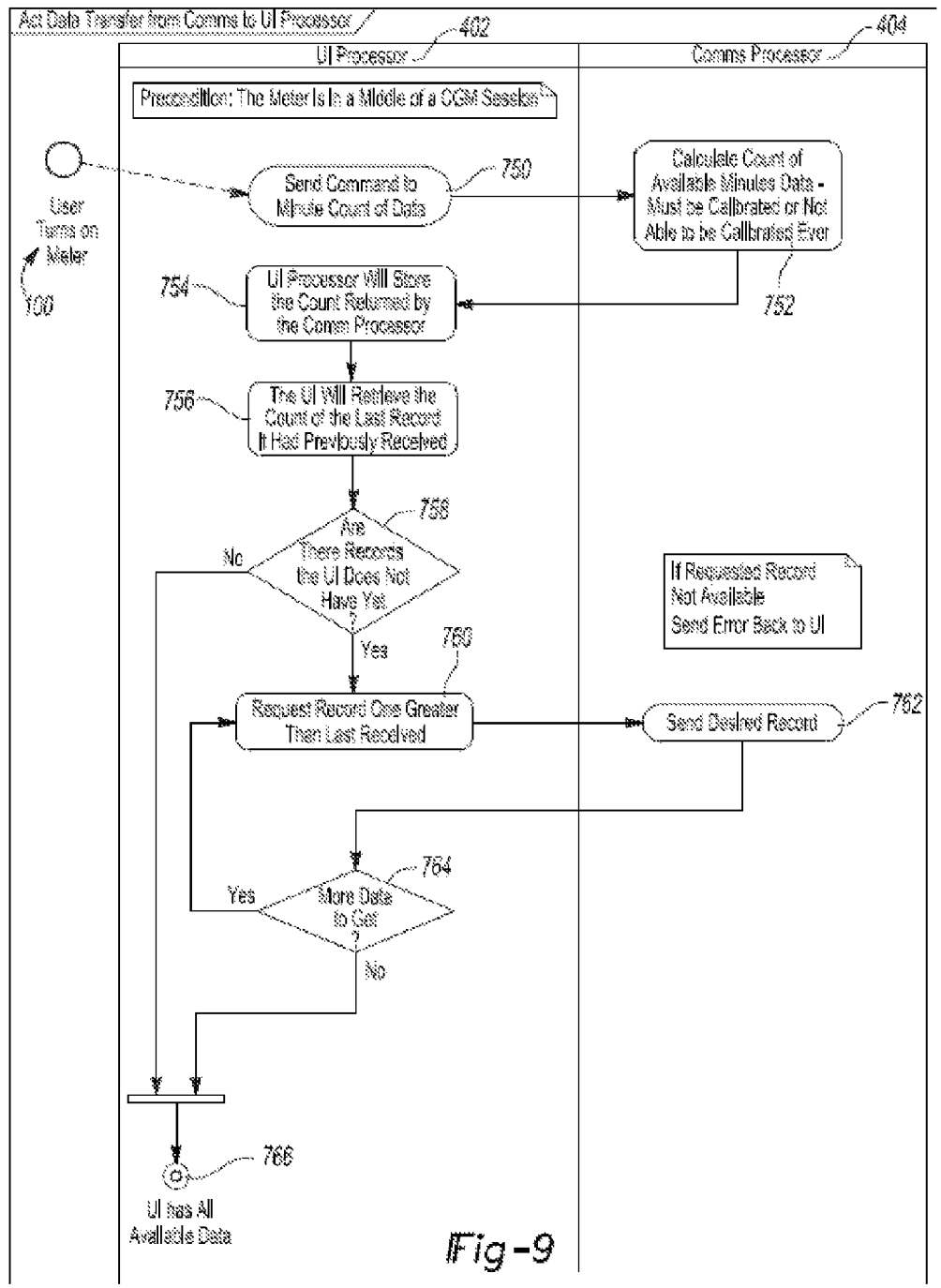
FIG. 9 is a functional flow diagram of an activity related to data transfer between a communications processor and a user interface processor of the diabetes manager of FIG. 3.
Figure 10A:
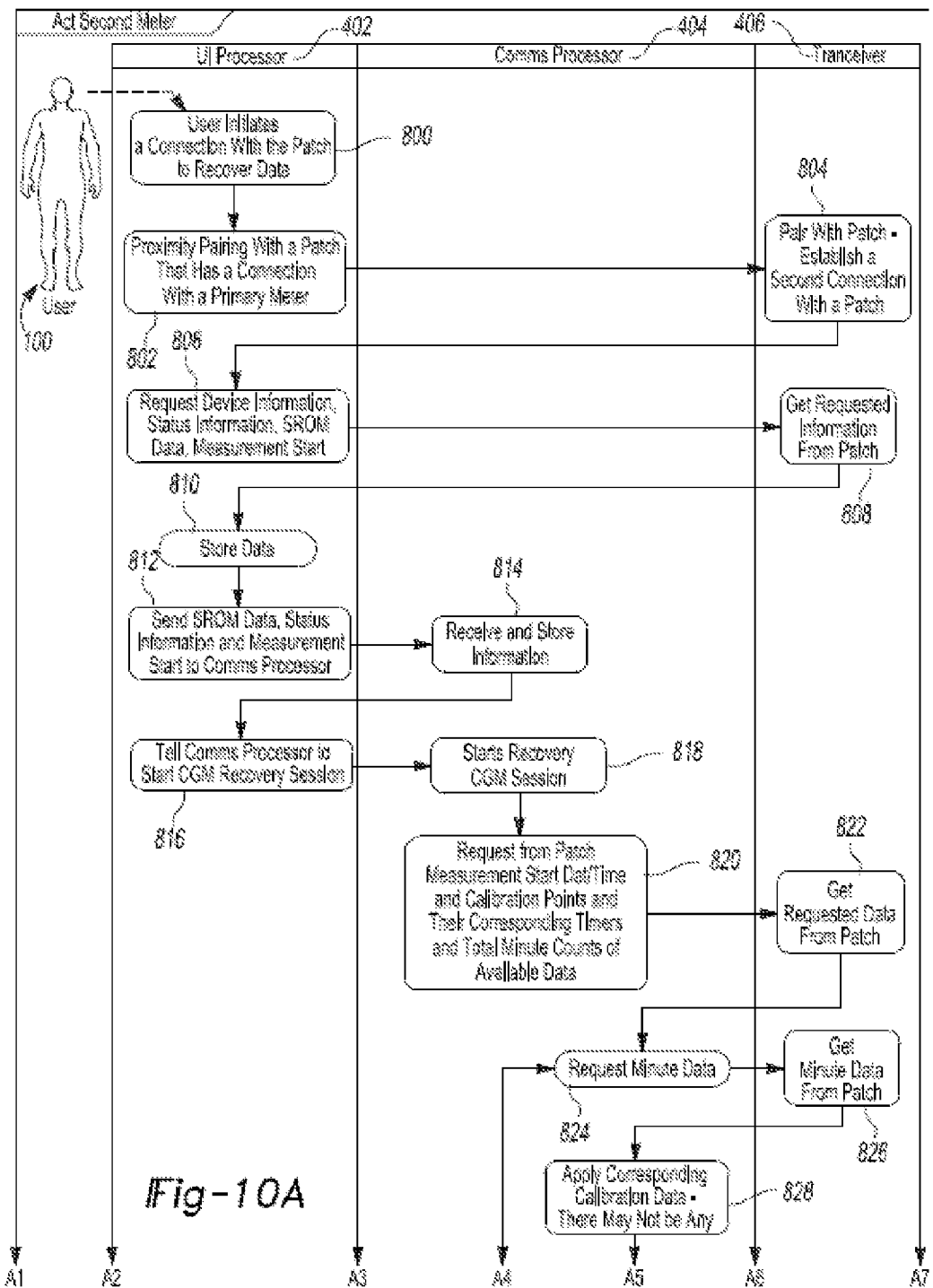
FIG. 10 (shown as FIG. 10A and FIG. 10B) is a functional flow diagram of an activity related to activating a second diabetes manager in addition to the diabetes manager of FIG. 3.
Figure 10B:
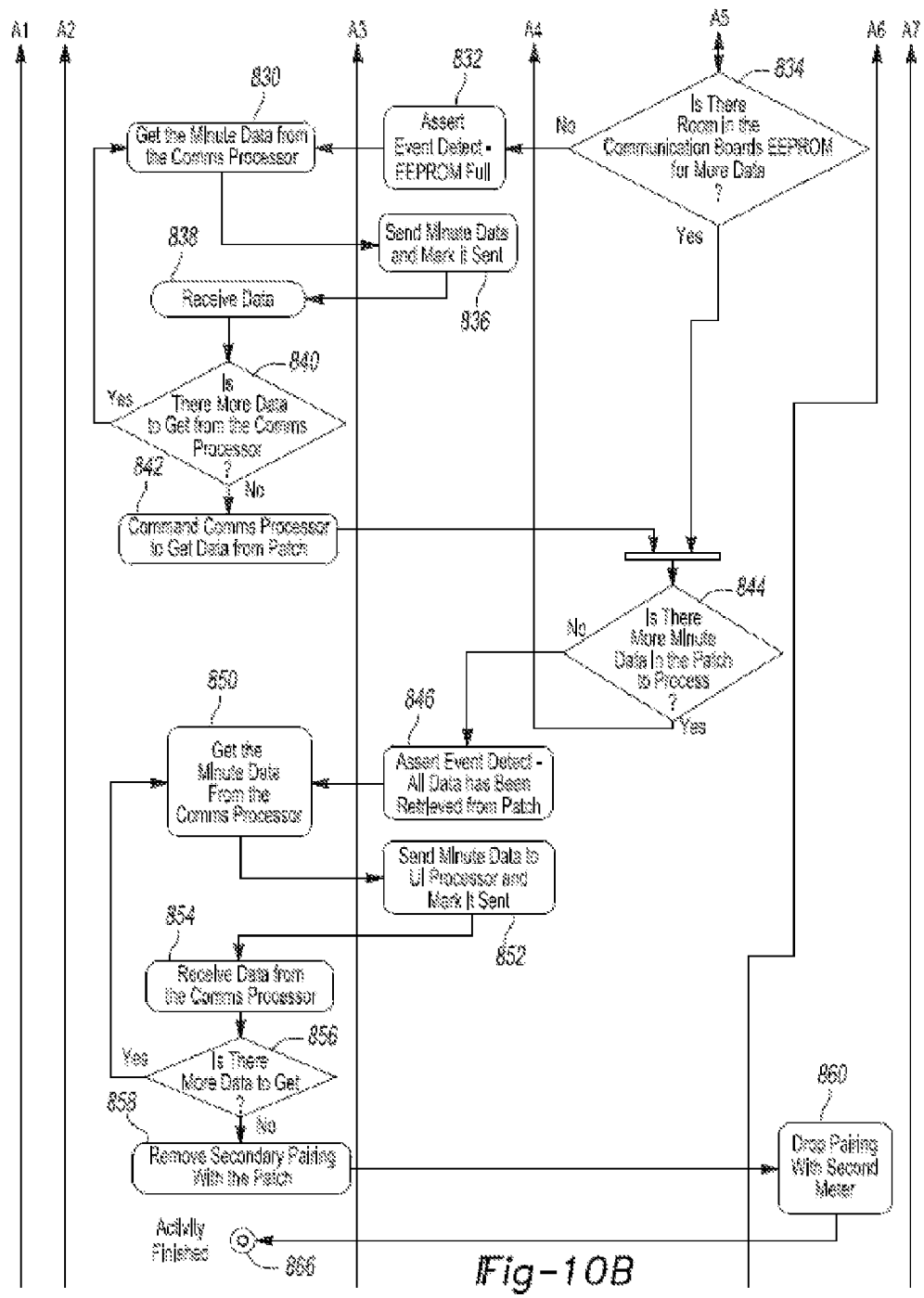

Referring now to FIGS. 5-10 various activities of the diabetes manager are described in reference to flow diagrams. A calibration activity is illustrated in FIG. 5 (including FIGS. 5A and 5B). A flow diagram for a Communications Processor Failure is illustrated in FIG. 6. A flow diagram for a Decision to Alert the UI processor 402 with CGM patch data is illustrated in FIG. 7. A flow diagram for Limit Checks is illustrated in FIG. 8. A flow diagram for Data transfer from the communications processor 404 to the UI processor 402 is illustrated in FIG. 9 A flow diagram for adding a second diabetes manager 104 is illustrated in FIG. 10 (including FIGS. 10A and 10B). The diabetes manager 104 is referenced as "meter" for short in the blocks of the flow diagrams of FIGS. 5-10.

Referring to FIG. 5 (FIGS. 5A and 5B), the interaction of the UI processor 402, the communications processor 404, and the CGM patch 200 is illustrated diagrammatically during a calibration activity. The calibration activity is an asynchronous activity in relation to the CGM patch 200. As discussed below, if warnings are enabled, the diabetes manager 104 requests minute data from the CGM patch 200 every minute. If warnings are not enabled, CGM data are obtained from the CGM patch 200 only when the diabetes manager 104 is in active mode (woken). Generally, when the CGM patch 200 is first paired and a CGM session is started, the CGM patch 200 is in a run-in or user acclimatization mode. This means that the CGM patch 200 is collecting data (in the form of current readings), but there is no filtering done on the collected data, and no glucose values are being derived from the corresponding currents. At the end of the run-in time, the user 100 performs a blood glucose (bG) test. The bG result from this test is used with the current readings from the CGM patch 200 to calibrate the CGM patch readings in the UI processor 402. The UI processor 402 sends calibration parameters (such as slope and intercept of the current) to the communications processor 404. These parameters are applied to all current readings that come into the communications processor 404 to convert the current readings to glucose readings or glucose values. These glucose readings are used for the calibration algorithms for the diabetes manager 104 and the CGM patch 200. The flow chart of FIG. 5 covers the ongoing calibration of the CGM patch 200 throughout its CGM session.

The UI processor 402 can be activated or woken up for several reasons including an alarm set to start calibration, a button pressed by the user 100 or a test strip inserted by the user 100 in the strip port 306 (FIG. 2) of the diabetes manager (meter) 104. The calibration activity is asynchronous. If hypo/hyper prediction warnings are enabled, the diabetes manager 104 attempts to obtain the CGM minute data every minute. If these warnings are not enabled, then the diabetes manager 104 communicates with the CGM patch 200 to obtain the CGM minute data only when the diabetes manager is on, i.e., woken up and in active mode.

As discussed above, the communications processor 404 collects minute data (at 504) from the CGM patch 200 (at 502) asynchronously relative to the UI processor 402. A record (or two records) of one hour (60 minutes) background data is retrieved and stored in the communications processor 404. Up to two such records are stored for each CGM session. Although more records can be stored, it is more efficient to use the UI processor for permanent storage, as discussed above. A CGM session is the time during which the CGM patch 200 can give continuous readings of CGM data without replacing its disposable or reusable components. When there are already two records and another third record is to be stored, the oldest record is overwritten. Additionally, there are two status registers in the minute data: the first is the device status at each respective minute data point and the second is the result of statistical fail-safe tests. If there is a non-zero status in either of these registers, i.e. if there is a non-zero entry in either of the two registers indicative of error, the communications processor 404 still stores the data packet from the CGM patch 200 and sets the glucose value to "invalid".

Referring specifically to FIG. 5A, when the diabetes manager (meter) 104 is powered on or woken up at 510, the UI processor 402 communicates with the communications processor 404 to request CGM data (FIG. 5A). The communications processor 404 checks for CGM data at 512 and returns the status and number of minute data available in the communications processor at 514. The status of the CGM data is checked at 516, and if there is an error regarding the CGM data, the error is handled by the communications processor 404 at 520 (Comms Error Handler) and transferred to the UI processor 402 at 522 (UI Error Handler) and the activity is terminated. Errors include CGM patch errors and other errors discussed in connection with FIG. 6 below. If there is no error in the CGM data, the communications processor 404 determines the number of minute data (how many minutes worth of CGM minute data) to retrieve at 524. Specifically, the minutes count in the diabetes manager 104 and the minute count in the CGM patch 200 is determined (at block 524) and compared at block 526. If the minutes count in the communications processor 404 is not less than the CGM patch count (at block 526), then the activity is terminated. If the minutes count in the communications processor 404 is equal to the minutes count in the UI processor 402 (at block 528) the activity is also terminated. If the minutes count in the communications processor 404 is less than the CGM patch count (at block 526), and if the minutes count in the communications processor 404 is not equal to the minutes count in the UI processor 402 (at block 528) then CGM minute data are obtained at block 530 from the CGM patch 200 using a low level command (such as a bus sniff command), at block 532, to maintain cache coherence. After the minute data are obtained at block 530, CGM calculations performed at block 534, followed by a query regarding the existence of additional minute data at block 536, whereupon if there are more CGM minute data the process returns to the block 530 to get the minute data. The process may have to wait for minute time to pass before checking for more minute data at 538.

Referring to the portion of the calibration activity illustrated in FIG. 5B, when the UI processor 402 detects that a strip inserted at block 550, it requests that all the radios (wireless communications with the CGM patch 200) are turned off at block 552 and the communications processor 404 commands the transceiver 406 to turn off the radios at 554. Thereafter, the bG test can be performed at block 556 and the bG result displayed for the user 100 at block 558. After the bG result is displayed, a command is issued at block 560 to turn the radio communication to the transceiver 406 and to resume communication with the CGM patch 200 at block 562. Communication with the CGM patch 200 is established and the CGM patch 200 is checked for more minute data at block 564. The CGM patch 200 resumes sending minute data at block 568, the communications processor 404 continues to get the CGM minute data at block 570 and perform calculations at block 572. A calibration error query is made at block 574 and if there is no calibration error, successful calibration is acknowledged at block 578 on the UI processor 402. If there is a calibration error, this information is reported to the error handler of the communications processor at 580. If there is no calibration error, the process continues in a loop as long as there are additional minute data (see block 576) and the activity stops when no more minute data are available.

Referring to FIG. 6, an activity diagram illustrates how communications processor errors are handled. Communications processor errors include communication errors with the CGM patch (block 602), i.e., connectivity errors between the communications processor and the CGM patch 200. Other errors include CGM patch errors (block 604) reported from the CGM patch 200 when the minute count and the status command is sent to the CGM patch 200. Other errors are hardware errors (block 606), which include failure of safety checks and inability to access different hardware on the communications processor board. Patch data processing errors (block 608) are also included in communication processor errors. Any of these errors is reported at 610 and the communications activity is ended at 616. From the error report at 610, the communications processor 404 asserts the Event Detect condition (block 612) to an Event Detect handler (block 614) of the UI processor 402. Details of the procedure for asserting the Event Detect condition are illustrated in FIG. 7 discussed below. The UI processor 402 sends an Event Detect Query Command (block 618) to determine the source or reason of the error. The communications processor 404 handles the Event Detect Command at block 620 and returns a Received Event Detect Query response to the UI processor 402 at block 622. The UI processor 402 requests a communication processor status at block 624, which the communications processor 404 returns at block 626, and the status is displayed at block 628 in the UI processor 402. The Event Detect activity ends at 630. As an additional safeguard, the UI processor 402 can periodically initiate error detection by requesting a communications processor status at block 632, which is responded to a block 634 of the communications processor 404 and displayed at block 636 in the UI processor 402. If there is no status response, failure is indicated at block 638 in the UI processor 402.

Referring to FIG. 7, a decision process for alerting the UI processor 402 with information regarding the CGM patch 200 is illustrated. The decision to alert process is called only after all the CGM patch data have been processed in the communications processor 404, regardless of the number of the minute data processed. Basically, the communications processor 404 checks for any reasons that trigger an Event Detect notification that needs to be communicated to the UI processor 402 immediately or can wait until the UI processor 402 is awake (in active mode). The decision to alert activity is related to the procedure to assert an Event Detect condition in block 612 of FIG. 6. Specifically, the decision to alert activity is called after all the data (one minute or many minutes of patch data) from the CGM patch 200 has been processed (at block 650). Post calculation safety checks are performed at block 652. The safety checks include a stack check of the communications processor 404, i.e., checking the memory stack of the communications processor for overflow problems, for example. If the safety checks fail (block 654) a non-recoverable hardware error is stored in a Cause Table of the Event Detect module 438 (FIG. 4) at block 656. In either case, the decision process continues to the next block 658 to query whether there is any cause stored in the Cause Table of the Event Detect module. If there is no cause stored, the activity ends at 670. If there is a cause stored in the Cause Table, the communications processor 404 queries whether the meter 104, i.e., the UI processor 402, is on active mode at block 660. If the UI processor is on active mode, the Event Detect condition is asserted at block 662 (corresponding to block 612 of FIG. 6). If the UI processor 402 is not in active mode, the next query at block 664 is to determine whether various warnings (low and high warnings, low prediction warnings). Depending on the answer, the next step is to examine the list of conditions or events that are set up in the UI processor 402 for waking up or not waking up the UI processor 402 in each case (warnings active or inactive). In block 666 the events that are set for waking up the UI processor 402 when the UI processor 402 is in sleep mode but the warnings are active are examined. The events examined in block 666 include, for example, the following: a warning threshold is crossed (high threshold, low threshold or low prediction threshold; see discussion of modules 450 and 452 of FIG. 4); the calibration state changes to "recommendation to calibrate" (see discussion of module 454 of FIG. 4); a status from the CGM patch 200 is non-zero (a non-zero entry); communication with the CGM patch 200 is lost; and an error is detected in the transceiver 406 or in the communications processor 404. In block 668 the events that are set for not waking up the UI processor 402 when the UI processor 402 is in sleep mode and the warnings are not active are examined. The events examined in block 668 include, for example, the following: the calibration state changes to "recommendation to calibrate" (see discussion of module 454 of FIG. 4); a status from the CGM patch 200 is non-zero; communication with the CGM patch 200 is lost; and an error is detected in the transceiver 406 or in the communications processor 404. When a corresponding event is detected in block 666, the UI processor is awakened with an Event Detect condition (block 662). When a corresponding event is detected in block 668, the UI processor 402 is notified with an Event Detect condition (block 662) the next time the UI processor 402 is in active mode.

Referring to FIG. 8, a flowchart of an activity that checks various time limits related to time block information is illustrated. The time block information includes generally a start time of daily data, an end time of daily data, a low bG level data value and a high bG level data value. In this respect, the time block data define a plurality of time windows, each of which can have a specified range of bG levels during the respective time window. The time block data are stored in the communications processor 404 but can be set and defined in the UI processor 402. The limit checks are set up in the UI processor 402, but are performed in the communications processor 404. Generally, the start time of the CGM session is known by both processors. The communications processor 404 also receives the minute count from the CGM patch 200 (block 732). The communications processor 404 receives the start time at the start of the CGM session, including the time block information (at block 720). The communications processor 404 converts the minute data to glucose values and applies filters at block 722 (as described above in relation to FIG. 4). The communication processor then uses a minute counter and determines the time block to which the processed data belong (at block 724).

The user 100 can make a time change (block 700) via the UI processor 402. The time change defines a time offset to the original start time of the CGM patch 200 and the time offset is sent to the communications processor (block 702). The new offset is stored in the communications processor (block 704). The time offset can be positive or negative. Additionally, the user 100 can change the time block limits using the UI processor 402 (block 706). The new time block definitions are sent to the communications processor 404 (block 708). The new time and new time block limits are stored to be applied to all new CGM patch data in the communications processor (block 710) and the activity ends at 712.

If the start time for the CGM session is changed in the UI processor 402 during the CGM session, the communications processor 404 receives a corresponding time offset at block 726 and continues the procedure of receiving and processing all the minute data from the CGM patch 200 via a loop of determining whether any minute data from the CGM patch 200 have not been processed yet (block 728) and requesting the next minute data from the CGM patch 200 (block 730).

The CGM patch data are sent to the communications processor 404 ((block 732) for glucose conversion and filtering at block 722.

Referring to FIG. 9, a flowchart of the activity of data transfer from the communications processor 404 to the UI processor 402 is illustrated. The data transferred to the UI processor 402 include run-in time data, calibrated data and non-calibrated data that it is to be calibrated. Data that can be calibrated is not sent to the UI processor 402. Run-in time data are data that are stored in the CGM pass during the run-in time, i.e., the time it takes for the CGM patch 200 to get acclimatized to the user 100. The flowchart of FIG. 9 illustrates the activity of data transfer while a CGM session is in progress. Specifically, when the user 100 activates the diabetes manager 104, the UI processor 402 sends a command to the communications process 404 to provide a minute count of data at block 750. The communications processor 404 calculates all the available data and sends only calibrated data and data that can no longer be calibrated (block 752). The UI processor 402 receives and stores the data received (block 754). The UI processor 402 retrieves the count of the last record of data previously received (block 756) and checks whether there are any records not yet received at block 758. If all records have been received, the UI processor 402 indicates that all available data are received at 766. Otherwise, the UI processor 402 sends a request to the communications processor 404 to provide a record numbered one greater than the record last received at block 760. The communications processor sends the requested record (block 762) to the UI processor 402. If the requested record is not available, the communications processor sends an error message to the UI processor 402. Block 764 initiates a loop requesting additional data until all the pertinent data are received from the communications processor 404.

Referring to FIG. 10 (shown as FIGS. 10A and 10B), a flow diagram of transferring data from the CGM patch 200 to a second diabetes manager 104 (or second meter 104) is illustrated. The second diabetes manager 104 can be, for example, a replacement diabetes manager device or a device used at a clinical setting. For clarity, the original diabetes meter 104 is referenced as first (primary) meter 104. The following preconditions apply for the transfer of data: the CGM patch 200 had an established relationship with the first meter 104, but not with the second meter 104; communication between the first meter 104 and the CGM patch 200 was not possible for a specified time; and communication between the second meter 104 and the CGM patch 200 is possible. The second meter 104 calibrates the CGM signal values exactly as the first meter 104. The first meter 104 sends the bG values, date and time of calibration to be stored in the CGM patch 200 and the second meter 104 recalculates the calibration coefficients in the same way and sequence as the first meter 104.

More specifically, the user 100 initiates a connection of the second meter 104 with the CGM patch 200 via the UI processor 402 of the second meter 104 to recover data (block 800). Proximity pairing is used with the CGM patch 200 (that has a connection with the first meter 104) at block 802. Pairing is established between the second meter 104 and the CGM patch 200 via the transceiver 406 at block 804. After connecting with the CGM patch 200, the UI processor 402 of the second meter 104 requests data including device information, status information, data stored in the memory of the CGM patch 200 (SROM data) and measurement start (block 806). The transceiver 406 obtains the requested information from the CGM patch 200 at block 808 and the data are stored in the UI processor 402 (block 810). The status information, SROM data and measurement start are sent from the UI processor 402 to the communications processor 404 (block 812) and stored in the communications processor 404 (block 814).

After this information is stored, the UI processor 402 instructs the communications processor 404 to initiate a CGM recovery session (block 816) and the communications processor 404 starts the CGM recovery session at block 818. A request is sent to the transceiver 406 to obtain from the CGM patch 200 measurement start date/time, calibration points and their corresponding timers and total minute counts of available data at block 820. The transceiver 406 gets the requested data from the CGM patch 200 at block 822. The communications processor 404 requests minute data at block 824 and the transceiver 406 gets minute data from CGM patch 200 at block 826. The communications processor 404 applies corresponding calibration data (if there are any) at block 828 and inquires whether there is space for storing more data in the memory (EEPROM) of the storage module of the communications processor 404 (block 834). If the memory is full, the communications processor 404 asserts the Event Detect condition that the memory is full at block 832. In response, the UI processor 402 requests minute data from the communications processor (block 830), the communications processor 404 sends the data and marks the data as sent at block 836. The UI processor 402 receives the data at block 838 and queries whether there are more minute data to be received from the communications processor 404 at block 840. If there are more minute data, a loop to get more minute data is started going back to block 830, otherwise the UI processor 402 commands the communications processor 404 to get more minute data from the CGM patch 200 at block 842. The communications processor 404 queries whether there more minute data in the CGM patch to be processed at block 844. If there are more data, a loop is initiated going back to block 824. If not, the communications processor asserts an Event Detect condition that all data has been retrieved from CGM patch 200 at block 846. The UI processor 402 then requests minute data from the communications processor 404 at block 850. The communications processor 404 sends the minute data to the UI processor 402 and marks the data as sent at block 852. The UI processor receives the minute data from the communications processor 404 at block 854, inquires whether there are more minute data at block 856. If yes, a loop starts again at block 850. If no, a request to remove pairing of the second meter 104 with the CGM patch is made at block 858, and the transceiver drops the pairing at block 860, whereupon the transfer activity ends at 866.

As used herein, the term module may refer to, be part of, or include an Application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above, such as in a system-on-chip. The term module may include memory (shared, dedicated, or group) that stores code executed by the processor.

The term code, as used above, may include software, firmware, and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

The apparatuses and methods described herein may be implemented by one or more computer programs executed by one or more processors. The computer programs include processor-executable instructions that are stored on a non-transitory tangible computer-readable medium. The computer programs may also include stored data. Non-limiting examples of the non-transitory tangible computer readable medium are nonvolatile memory, magnetic storage, and optical storage.

The broad teachings of the disclosure can be implemented in a variety of forms. Therefore, while this disclosure includes particular examples, the scope of the disclosure should not be so limited since other modifications will become apparent to the skilled practitioner upon a study of the drawings, the specification, and the following claims.

What is claimed is:

1. A handheld diabetes management device for managing blood glucose test data and continuous glucose monitoring data, comprising:
a port residing in the handheld diabetes management device and configured to receive a test strip;
a wireless transceiver;
a communications processor cooperatively operable with the wireless transceiver to periodically collect glucose measurement data from a continuous glucose monitoring device and to store the glucose measurement data in a first data storage module, the communications processor being operable to consume electrical power at a first rate; and
a user interface processor in data communication with the communication processor, wherein the user interface processor operates in an active mode to retrieve and process the glucose measurement data from the communication processor and operates in a low power mode asynchronously from the communications processor;
wherein the communication processor detects a trigger condition and, in response to the trigger condition, wakes up the user interface processor from the low power mode to the active mode, such that the user interface processor consumes electrical power in the active mode at a higher rate than the first rate and the user interface processor consumes electrical power in the low power mode at a lower rate than the first rate.

2. The diabetes management device of claim 1, wherein the user interface processor controls blood glucose measurements from the test strip and the communications processor performs calibration using the blood glucose measurements.

3. The diabetes management device of claim 1, wherein the user interface processor includes a second data storage module that receives glucose measurement data from the first storage module and the received data are deleted from the first data storage module.

4. The diabetes management device of claim 1, wherein the communications processor has a timer that operates to activate the communications processor to retrieve the continuous glucose monitoring data.

5. The diabetes management device of claim 1, wherein when a test strip is inserted in the port, the communication processor operates to turn the transceiver off.

6. The diabetes management device of claim 1, wherein the communications processor wakes up the user interface processor from a sleep mode when safety warnings are active and a warning threshold is crossed.

7. The diabetes management device of claim 1, wherein the communications processor wakes up the user interface processor from a sleep mode when safety warnings are active and calibration is recommended.

8. The diabetes management device of claim 1, wherein the communications processor wakes up the user interface processor from a sleep mode when safety warnings are active and a communication error is detected in the transceiver or communications processor.

9. The diabetes management device of claim 1, wherein the communications processor wakes up the user interface processor from a sleep mode when safety warnings are active and communication with continuous glucose monitoring device is lost.

10. The diabetes management device of claim 1, wherein the communications processor does not wake up the user interface processor from a sleep mode when safety warnings are not active and any of the following events is detected:
recommendation to calibrate; a communication error in the transceiver or communications processor; and a non-zero status indicative of error from the continuous glucose monitoring device.

11. The diabetes management device of claim 10, wherein the communications processor stores the detected event and notifies the user interface processor when the user interface processor is in active mode.

12. The diabetes management device of claim 1, wherein the user interface processor sends time offsets and time block limits to the communications processor and the communications processor applies the time offsets and time block limits to the data from the continuous glucose monitoring device.

13. The diabetes management device of claim 1, wherein the interface processor initiates pairing with the continuous glucose monitoring device that has been in communication with a different diabetes management device and directs the communications processor to retrieve data from the continuous glucose monitoring device for storage in the user interface processor.

* * * * *